United States Patent
Zheng

(10) Patent No.: US 9,923,145 B2
(45) Date of Patent: Mar. 20, 2018

(54) 3,5-BIS(10-NAPHTHALENYL-ANTHRACEN-9-YL)PYRIDINE COMPOUNDS AS HOSTS FOR LIGHT-EMITTING DEVICES

(71) Applicant: Nitto Denko Corporation, Osaka (JP)

(72) Inventor: Shijun Zheng, San Diego, CA (US)

(73) Assignee: NITTO DENKO CORPORATION, Osaka (JP)

( * ) Notice: Subject to any disclaimer, the term of this patent is extended or adjusted under 35 U.S.C. 154(b) by 573 days.

(21) Appl. No.: 14/384,275

(22) PCT Filed: Mar. 12, 2013

(86) PCT No.: PCT/US2013/030570
§ 371 (c)(1),
(2) Date: Sep. 10, 2014

(87) PCT Pub. No.: WO2013/138365
PCT Pub. Date: Sep. 19, 2013

(65) Prior Publication Data
US 2015/0041733 A1   Feb. 12, 2015

Related U.S. Application Data

(60) Provisional application No. 61/610,038, filed on Mar. 13, 2012.

(51) Int. Cl.
*H01L 51/00* (2006.01)
*C09K 11/06* (2006.01)
*C07D 213/24* (2006.01)
*H01L 51/50* (2006.01)

(52) U.S. Cl.
CPC ........ *H01L 51/0058* (2013.01); *C07D 213/24* (2013.01); *C09K 11/06* (2013.01); *H01L 51/0067* (2013.01); *C09K 2211/185* (2013.01); *H01L 51/0064* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 6,797,848 B2 | 9/2004 | Hosokawa et al. | |
| 2009/0108746 A1 | 4/2009 | Park et al. | |
| 2009/0166670 A1 | 7/2009 | Park et al. | |
| 2011/0306922 A1 | 12/2011 | Khan et al. | |
| 2012/0193614 A1* | 8/2012 | Zheng | C09K 11/06 257/40 |
| 2015/0014671 A1* | 1/2015 | Koike | C07D 401/10 257/40 |

FOREIGN PATENT DOCUMENTS

| | | |
|---|---|---|
| JP | 2009209133 | 9/2009 |
| WO | WO 2007065678 | 6/2007 |
| WO | WO 2010114263 | 10/2010 |

\* cited by examiner

*Primary Examiner* — Dawn L Garrett
(74) *Attorney, Agent, or Firm* — K&L Gates LLP; Louis C. Cullman; Robert W. Winn

(57) ABSTRACT

Optionally substituted 3-(10-(aryl)anthracen-9-yl)-5-(10-(aryl)anthracen-9-yl)pyridine compounds may be used as host compounds for devices such as organic light-emitting devices.

27 Claims, 1 Drawing Sheet

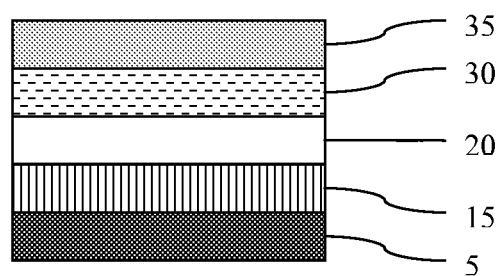

3,5-BIS(10-NAPHTHALENYL-ANTHRACEN-9-YL)PYRIDINE COMPOUNDS AS HOSTS FOR LIGHT-EMITTING DEVICES

CROSS REFERENCE TO RELATED APPLICATIONS

This application is a national phase of PCT/US2013/030570 filed on Mar. 12, 2013, which claims the benefit of U.S. Provisional Patent Application No. 61/610,038, filed Mar. 13, 2012, which is incorporated by reference herein in its entirety.

FIELD OF THE DISCLOSURE

The embodiments disclosed herein relate to host compounds for light-emitting layers in devices.

BACKGROUND

Organic light-emitting devices (OLED) are becoming increasingly important in lighting and display applications. OLEDs may include an emissive or light-emitting layer that includes a host material and an emissive component dispersed within the host material. Host material OLED devices may have problems with low stability, a high charge-injection barrier, and imbalanced charge injection and mobilities. These potential deficiencies with host materials may contribute to low efficiency and short lifetime of the devices comprising the host materials.

SUMMARY OF THE DISCLOSURE

Some embodiments include a compound represented by Formula 1:

$$Ht^1-A^1-Py-A^2-Ht^2 \quad \text{Formula 1}$$

wherein Py is optionally substituted pyridin-3,5-yl; $A^1$ and $A^2$ are independently optionally substituted anthracen-9,10-yl; and $Ht^1$ and $Ht^2$ are independently optionally substituted phenyl, optionally substituted pyridinyl, optionally substituted naphthylenyl, optionally substituted biphenyl, optionally substituted carbazolyl, —NRR°, or -Ph-NRR°, wherein Ph is optionally substituted phenyl, and R and R° are independently optionally substituted $C_{6-10}$ aryl.

Some embodiments include a compound represented by Formula 1, wherein Py is pyridin-3,5-yl optionally substituted with 1 or 2 substituents selected from: F, methyl, ethyl, and phenyl; $A^1$ and $A^2$ are independently anthracen-9,10-yl optionally substituted with 1 or 2 substituents selected from: F, methyl, ethyl, and phenyl; and $Ht^1$ and $Ht^2$ are independently naphthylen-2-yl optionally substituted with 1 or 2 substituents selected from: F, methyl, ethyl, and phenyl; wherein each phenyl is unsubstituted, or has 1 or 2 substituents independently selected from F, methyl, and ethyl.

Some embodiments include optionally substituted 3-(10-(naphthalen-2-yl)anthracen-9-yl)-5-(10-(naphthalen-3-yl)anthracen-9-yl)pyridine.

Some embodiments include a light-emitting device comprising a compound described herein.

These and other embodiments are described in more detail herein.

BRIEF DESCRIPTION OF THE DRAWINGS

The FIGURE is a schematic depiction of an embodiment of an organic light-emitting device.

DETAILED DESCRIPTION

Unless otherwise indicated, where a compound or chemical structural feature such as aryl is referred to herein as being "optionally substituted," it includes a feature that has no substituents (i.e., unsubstituted), or a feature that is "substituted," meaning that the feature has one or more substituents. The term "substituent" has the ordinary meaning known to one of ordinary skill in the art, and includes a moiety that replaces one or more hydrogen atoms attached to a parent compound or structural feature. In some embodiments, the substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, the substituent comprises: 0-30, 0-20, 0-10, or 0-5 carbon atoms; and, 0-30, 0-20, 0-10, or 0-5 heteroatoms independently selected from N, O, S, Si, F, Cl, Br, or I; provided that the substituent comprises at least one atom selected from C, N, O, S, Si, F, Cl, Br, or I. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

Structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by -|, attachment may occur at any position normally occupied by a hydrogen atom.

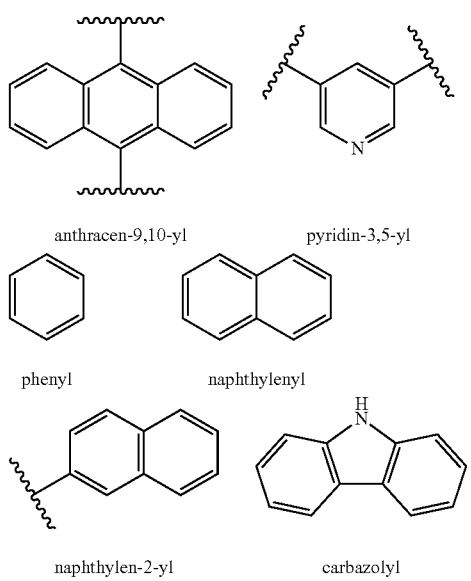

anthracen-9,10-yl    pyridin-3,5-yl phenyl    naphthylenyl naphthylen-2-yl    carbazolyl

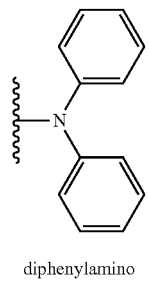
diphenylamino

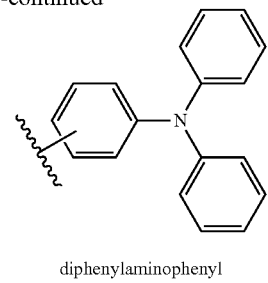
diphenylaminophenyl

pyridinyl

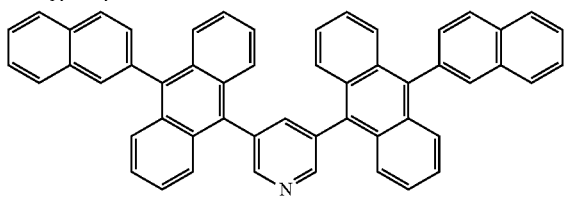
3-(10-(naphthalen-2-yl)anthracen-9-yl)-5-(10-(naphthalen-3-yl)anthracen-9-yl)pyridine As used herein, the term "aryl" has the broadest meaning generally understood in the art, and may include an aromatic ring or aromatic ring system such as phenyl, naphthyl, etc. The term "heteroaryl" also has the meaning understood by a person of ordinary skill in the art, and in some embodiments, may refer to an "aryl" which has one or more heteroatoms in the ring or ring system. Examples of "heteroaryl" may include, but are not limited to, pyridinyl, furyl, thienyl, oxazolyl, thiazolyl, imidazolyl, indolyl, quinolinyl, benzofuranyl, benzothienyl, benzooxazolyl, benzothiazolyl, benzoimidazolyl, etc.

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g., branched pentyl isomers), $C_6H_{13}$ (e.g. branched hexyl isomers), $C_7H_{15}$ (e.g., heptyl isomers), etc.; $C_{3-10}$ cycloalkyl, such as $C_3H_5$ (e.g. cyclopropyl), $C_4H_7$ (e.g., cyclobutyl isomers such as cyclobutyl, methylcyclopropyl, etc.), $C_5H_9$ (e.g., cyclopentyl isomers such as cyclopentyl, methylcyclobutyl, dimethylcyclopropyl, etc.), $C_6H_{11}$ (e.g., cyclohexyl isomers), $C_7H_{13}$ (e.g. cycloheptyl isomers), etc.; and, the like.

As used herein, the term "alkoxy" includes —O-alkyl, such as —$OCH_3$, —$OC_2H_5$, —$OC_3H_7$ (e.g., propoxy isomers such as isopropoxy, n-propoxy, etc.), —$OC_4H_9$ (e.g., butyoxy isomers), —$OC_5H_{11}$ (e.g., pentoxy isomers), —$OC_6H_{13}$ (e.g., hexoxy isomers), —$OC_7H_{15}$ (e.g., heptoxy isomers), etc.

Some embodiments include a compound according to any one of Formulas 2-8.

Formula 2

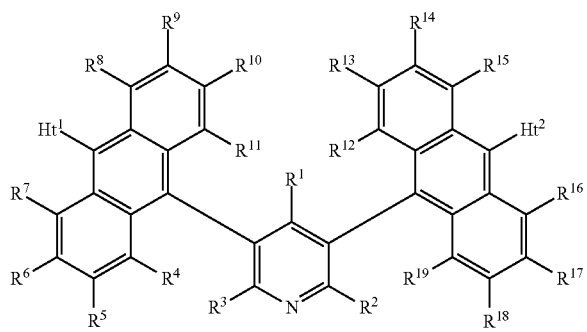

Formula 3

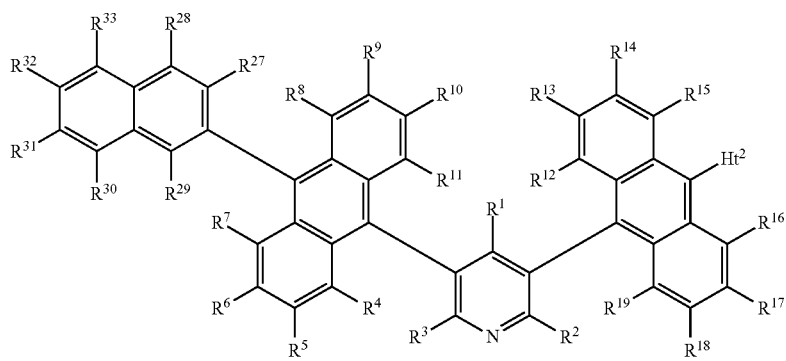

Formula 4
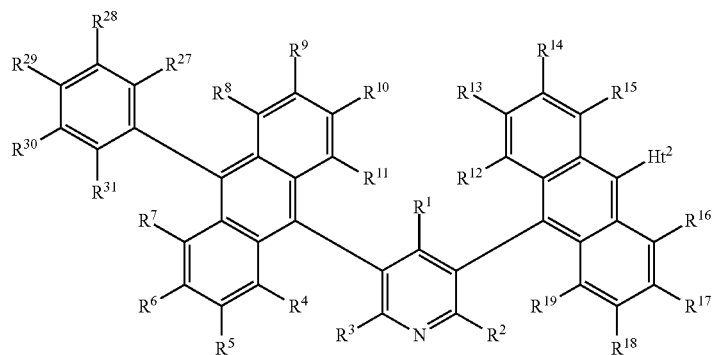
Formula 5
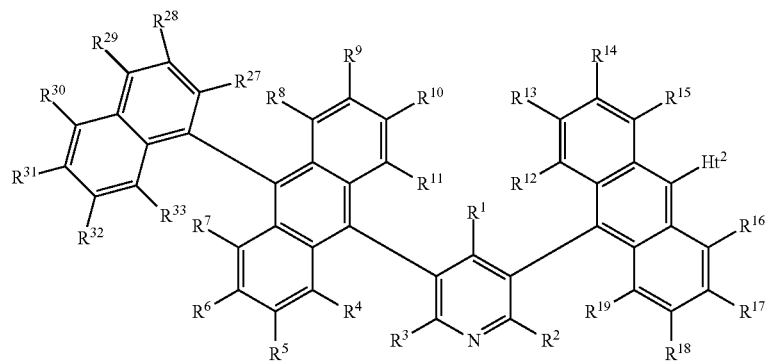
Formula 6
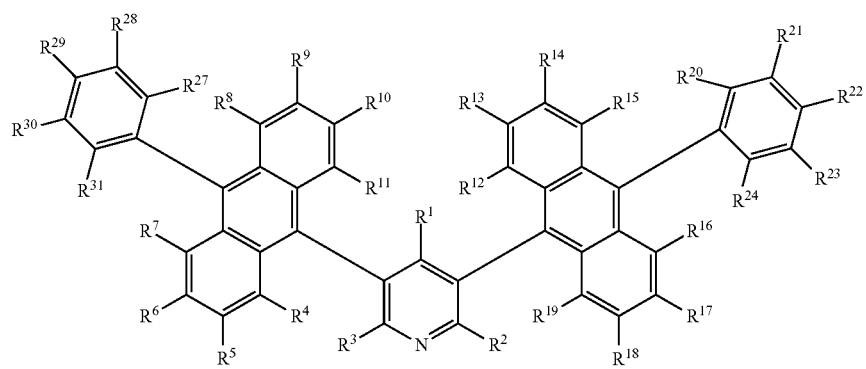
Formula 7
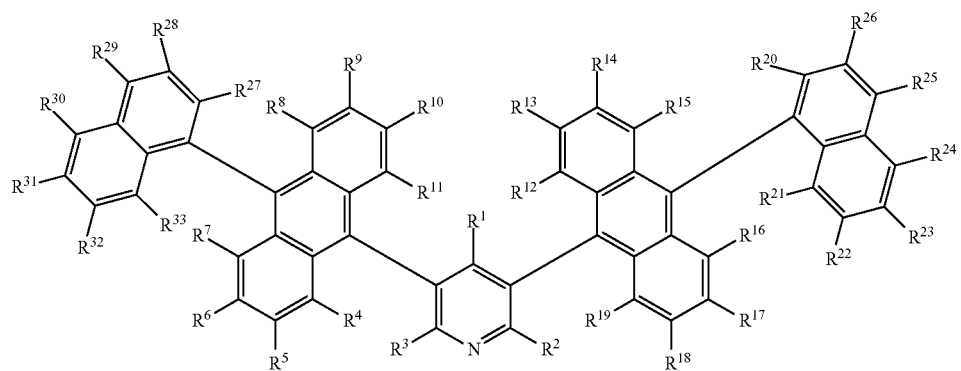

-continued

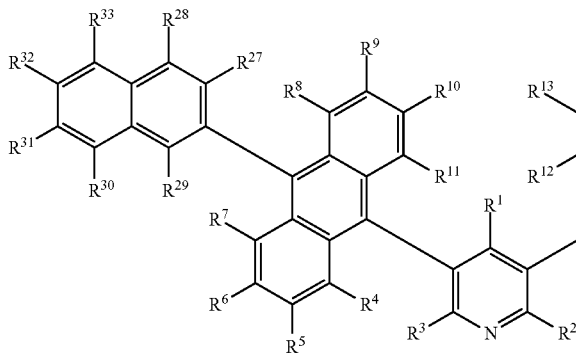
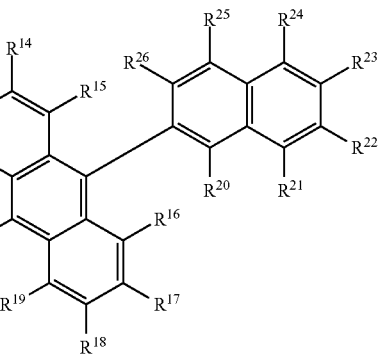

Formula 8

With respect to any relevant formula or structural depiction above, Py may be optionally substituted pyridin-3,5-yl. In some embodiments, if the pyridin-3,5-yl is substituted, it may have 1, 2, 3, or 4 substituents. Any substituent may be included on the pyridin-3,5-yl. In some embodiments, some or all of the substituents on the pyridin-3,5-yl may have: from 0 to 10 carbon atoms and from 0 to 10 heteroatoms independently selected from O, N, S, F, Cl, Br, and I; and/or, a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, or I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or, a $C_{1-10}$ amine such as $NH_2$, $NH(CH_3)$, $N(CH_3)_2$, $N(CH_3)C_2H_5$, etc. In some embodiments, Py is optionally substituted with 1 or 2 substituents independently selected from F, methyl, ethyl, and phenyl, wherein each phenyl is unsubstituted, or has 1 or 2 substituents independently selected from F, methyl, and ethyl. In some embodiments, Py is unsubstituted.

In some embodiments, Py is:

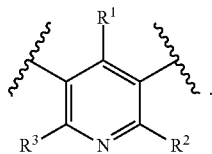

With respect to any relevant formula or structural depiction above, $A^1$ may be optionally substituted anthracen-9,10-yl. In some embodiments, if the anthracen-9,10-yl is substituted, it may have 1, 2, 3, or 4 substituents. Any substituent may be included on the anthracen-9,10-yl. In some embodiments, some or all of the substituents on the anthracen-9,10-yl may have: from 0 to 10 carbon atoms and from 0 to 10 heteroatoms independently selected from O, N, S, F, Cl, Br, and I; and/or, a molecular weight of 15 g/mol to 500 g/mol. For example, the substituents may be $C_1$-10 alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, or I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; a $C_{1-10}$ amine such as $NH_2$, $NH(CH_3)$, $N(CH_3)_2$, $N(CH_3)C_2H_5$, etc.; or phenyl, wherein each phenyl is unsubstituted, or has 1 or 2 substituents independently selected from F and $C_{1-6}$ alkyl. In some embodiments, $A^1$ is optionally substituted with 1 or 2 substituents independently selected from F, methyl, ethyl, and phenyl, wherein each phenyl is unsubstituted, or has 1 or 2 substituents independently selected from F, methyl, and ethyl. In some embodiments, $A^1$ is unsubstituted.

In some embodiments, $A^1$ is:

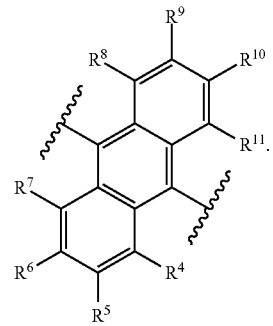

With respect to any relevant formula or structural depiction above, $A^2$ may be optionally substituted anthracen-9,10-yl. In some embodiments, if the anthracen-9,10-yl is substituted, it may have 1, 2, 3, or 4 substituents. Any substituent may be included on the anthracen-9,10-yl. In some embodiments, some or all of the substituents on the anthracen-9,10-yl may have: from 0 to 10 carbon atoms and from 0 to 10 heteroatoms independently selected from O, N, S, F, Cl, Br, and I; and/or, a molecular weight of 15 g/mol to 500 g/mol. For example, the substituents may be $C_1$-10 alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, or I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; a $C_{1-10}$ amine such as $NH_2$, $NH(CH_3)$, $N(CH_3)_2$, $N(CH_3)C_2H_5$, etc.; or phenyl, wherein each phenyl is unsubstituted, or has 1 or 2 substituents independently selected from F and $C_{1-6}$ alkyl. In some embodiments, $A^2$ is optionally substituted with 1 or 2 substituents independently selected from F, methyl, ethyl, and phenyl, wherein each phenyl is unsubstituted, or has 1 or 2 substituents independently selected from F, methyl, and ethyl. In some embodiments, $A^2$ is unsubstituted.

In some embodiments, $A^2$ is:

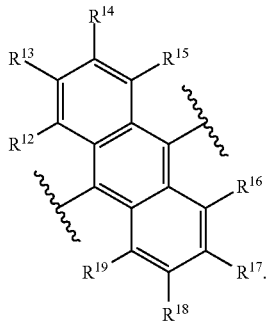

With respect to any relevant formula or structural depiction above, $Ht^1$ may be optionally substituted phenyl, optionally substituted pyridinyl, optionally substituted naphthylenyl, optionally substituted biphenyl, optionally substituted carbazolyl, —$NRR^\circ$, or -Ph-$NRR^\circ$, wherein Ph is optionally substituted phenyl, and R and $R^\circ$ are independently optionally substituted $C_{6-10}$ aryl. In some embodiments, if $Ht^1$ is substituted, it may have 1, 2, 3, or 4 substituents. Any substituent may be included on $Ht^1$. In some embodiments, some or all of the substituents on $Ht^1$, including those on Ph, R, and $R^\circ$, may have: from 0 to 10 carbon atoms and from 0 to 10 heteroatoms independently selected from O, N, S, F, Cl, Br, and I; and/or, a molecular weight of 15 g/mol to 500 g/mol. For example, the substituents may be $C_1$-10 alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, or I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; a $C_{1-10}$ amine such as $NH_2$, $NH(CH_3)$, $N(CH_3)_2$, $N(CH_3)C_2H_5$, etc.; or phenyl, wherein each phenyl is unsubstituted, or has 1 or 2 substituents independently selected from F and $C_{1-6}$ alkyl. In some embodiments, $Ht^1$ is optionally substituted with 1 or 2 substituents independently selected from F, methyl, ethyl, and phenyl, wherein each phenyl is unsubstituted, or has 1 or 2 substituents independently selected from F, methyl, and ethyl. In some embodiments, $Ht^1$ is unsubstituted.

In some embodiments, $Ht^1$ may be:

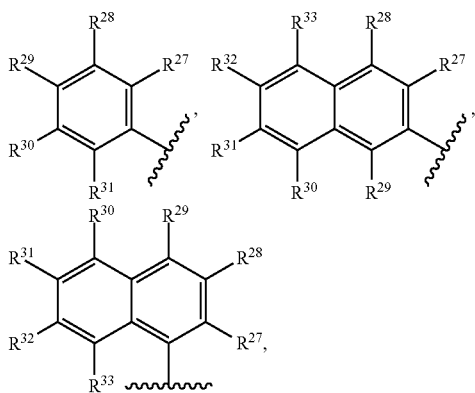

-continued

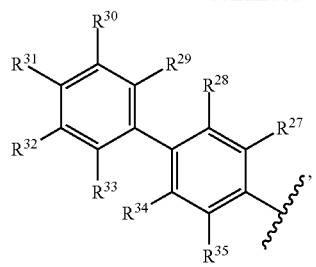

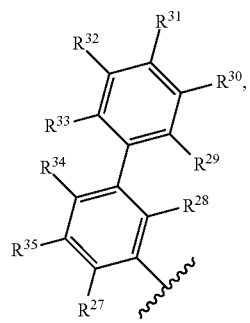

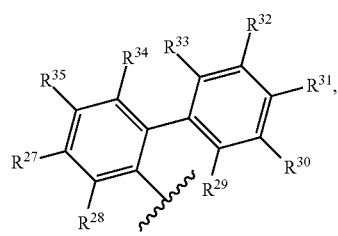

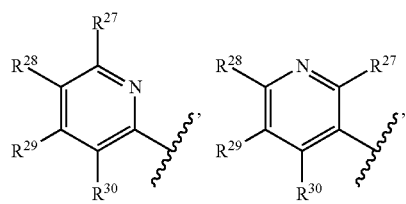

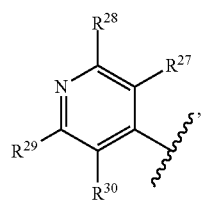

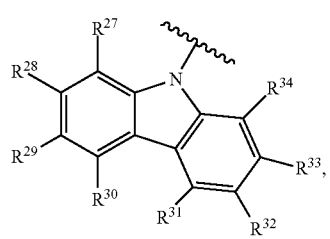

-continued

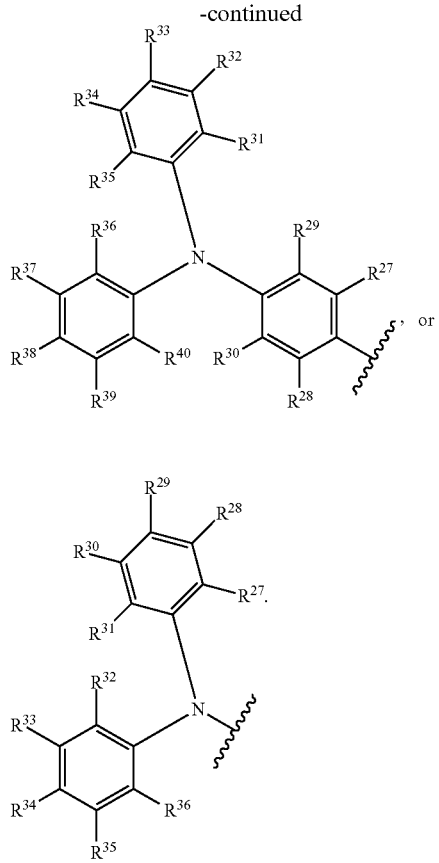

With respect to any relevant formula or structural depiction above, $Ht^2$ may be optionally substituted phenyl, optionally substituted pyridinyl, optionally substituted naphthylenyl, optionally substituted biphenyl, optionally substituted carbazolyl, $-NRR°$, or $-Ph-NRR°$, wherein Ph is optionally substituted phenyl, and R and R° are independently optionally substituted $C_{6-10}$ aryl. In some embodiments, if $Ht^2$ is substituted, it may have 1, 2, 3, or 4 substituents. Any substituent may be included on $Ht^2$. In some embodiments, some or all of the substituents on $Ht^2$, including those on Ph, R, and R°, may have: from 0 to 10 carbon atoms and from 0 to 10 heteroatoms independently selected from: O, N, S, F, Cl, Br, and I; and/or, a molecular weight of 15 g/mol to 500 g/mol. For example, the substituents may be $C_{1}$-10 alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, or I; OH; CN; $NO_2$; $C_{1-6}$ fluoroalkyl, such as $CF_3$, $CF_2H$, $C_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; a $C_{1-10}$ amine such as $NH_2$, $NH(CH_3)$, $N(CH_3)_2$, $N(CH_3)C_2H_5$, etc.; or phenyl, wherein each phenyl is unsubstituted, or has 1 or 2 substituents independently selected from F and $C_{1-6}$ alkyl. In some embodiments, $Ht^2$ is optionally substituted with 1 or 2 substituents independently selected from F, methyl, ethyl, and phenyl, wherein each phenyl is unsubstituted, or has 1 or 2 substituents independently selected from F, methyl, and ethyl. In some embodiments, $Ht^2$ is unsubstituted.

In some embodiments, $Ht^2$ may be:

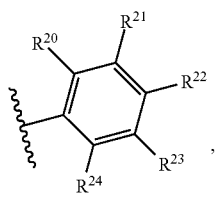

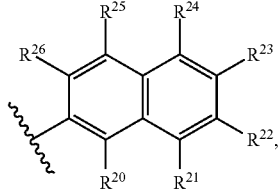

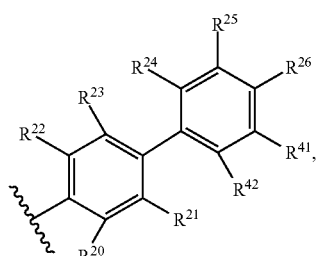

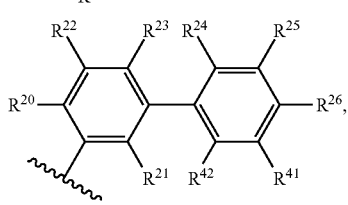

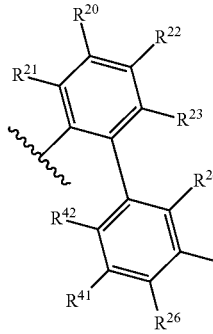

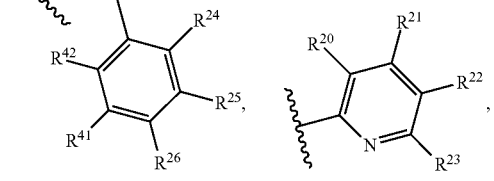

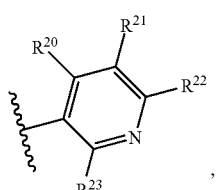

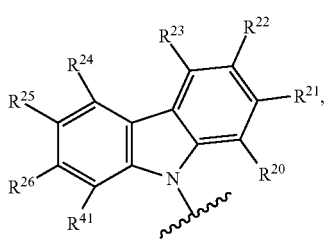

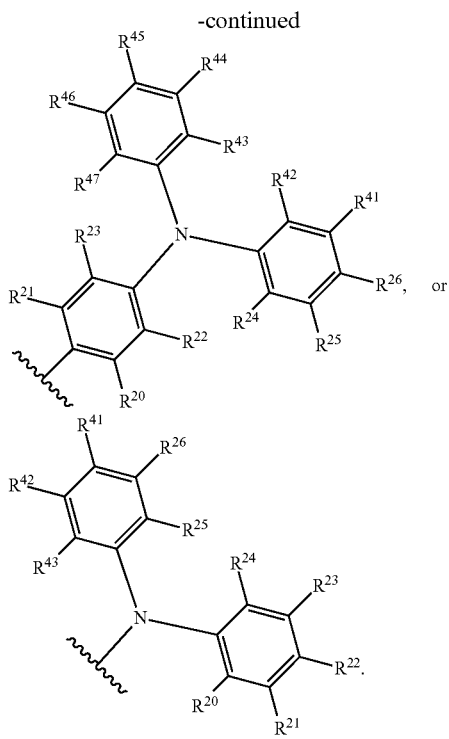

In some embodiments, Py is unsubstituted, or all substituents of Py have a molecular weight of about 15 g/mol to about 150 g/mol; $A^1$ is unsubstituted, or all substituents of $A^1$ have a molecular weight of about 15 g/mol to about 150 g/mol; $A^2$ is unsubstituted, or all substituents of $A^2$ have a molecular weight of about 15 g/mol to about 150 g/mol; $Ht^1$ is unsubstituted, or all substituents of $Ht^1$ have a molecular weight of about 15 g/mol to about 150 g/mol; and/or $Ht^2$ is unsubstituted, or all substituents of $Ht^2$ have a molecular weight of about 15 g/mol to about 150 g/mol.

R may be optionally substituted aryl, including optionally substituted phenyl, optionally substituted biphenyl, and optionally substituted naphthyl. In some embodiments, substituents of R may include may include $R^A$, F, Cl, CN, $OR^A$, $CF_3$, $NO_2$, $NR^AR^B$, $COR^A$, $CO_2R^A$, $OCOR^A$, etc. In some embodiments, any substituents may be F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, any substituents of R may independently be F, methyl, ethyl, propyl, isopropyl, or phenyl, wherein each phenyl is independently unsubstituted, or has 1 or 2 substituents independently selected from F, methyl, ethyl, propyl, and isopropyl. In some embodiments, R may be unsubstituted phenyl.

$R^o$ may be optionally substituted aryl, including optionally substituted phenyl, optionally substituted biphenyl and optionally substituted naphthyl. In some embodiments, substituents of $R^o$ may include may include $R^A$, F, Cl, CN, $OR^A$, $CF_3$, $NO_2$, $NR^AR^B$, $COR^A$, $CO_2R^A$, $OCOR^A$, etc. In some embodiments, any substituents may be F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, any substituents of $R^o$ may independently be F, methyl, ethyl, propyl, isopropyl, or phenyl, wherein each phenyl is independently unsubstituted, or has 1 or 2 substituents independently selected from F, methyl, ethyl, propyl, and isopropyl. In some embodiments, $R^o$ may be unsubstituted phenyl.

Generally $R^1$-$R^{47}$ may be H or any substituent, such as a substituent having from 0 to 6 carbon atoms and from 0 to 5 heteroatoms independently selected from: O, N, S, F, Cl, Br, and I, and/or having a molecular weight of 15 g/mol to 300 g/mol. Any of $R^1$-$R^{47}$ may comprise: a) 1 or more alkyl moieties optionally substituted with, or optionally connected by, b) 1 or more functional groups, such as C=C, C≡C, CO, $CO_2$, CON, $NCO_2$, OH, O, S, N, N=C, F, Cl, Br, I, CN, $NO_2$, $CO_2H$, $NH_2$, etc. Alternatively, any of $R^1$-$R^{44}$ may be substituent having no alkyl portion, such as F, Cl, Br, I, $NO_2$, CN, $NH_2$, OH, COH, $CO_2H$, etc.

With respect to any relevant formula or structural depiction above, some non-limiting examples of $R^1$ may include $R^A$, F, Cl, CN, $OR^A$, $CF_3$, $NO_2$, $NR^AR^B$, $COR^A$, $CO_2R^A$, $OCOR^A$, etc. In some embodiments, $R^1$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^1$ may be independently H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^1$ may be H.

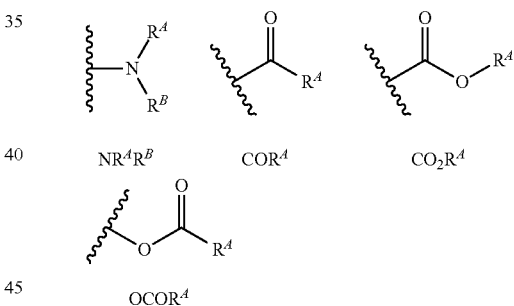

Each $R^A$ may independently be H; $C_{1-12}$ alkyl, including: linear or branched alkyl having a formula $C_aH_{a+1}$, or cycloalkyl having a formula $C_aH_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.; or optionally substituted phenyl, wherein any substituents on the phenyl may include $R^C$, F, Cl, CN, $OR^C$, $CF_3$, $NO_2$, $NR^CR^D$, $COR^C$, $CO_2R^C$, $OCOR^C$, etc.

Each $R^B$ may independently be H; $C_{1-12}$ alkyl, including: linear or branched alkyl having a formula $C_aH_{a+1}$, or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.; or optionally substituted phenyl, wherein any substituents on the phenyl may include: $R^C$, F, Cl, CN, $OR^D$, $CF_3$, $NO_2$, $NR^CR^D$, $COR^D$, $CO_2R^D$, $OCOR^D$, etc.

Each $R^C$ may independently be H; $C_{1-12}$ alkyl, including: linear or branched alkyl having a formula $C_aH_{a+1}$; or, cycloalkyl having a formula $C_aH_{a-1}$, wherein a is 1, 2, 3, 4, 5, 6, 7, 8, 9, 10, 11, or 12, such as linear or branched alkyl of a formula $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc.; or, cycloalkyl of a formula $C_3H_5$, $C_4H_7$, $C_5H_9$, $C_6H_{11}$, $C_7H_{13}$, $C_8H_{15}$, $C_9H_{17}$, $C_{10}H_{19}$, etc.

Each $R^D$ may independently be H; $C_{1-12}$ alkyl, including: linear or branched alkyl having a formula $C_aH_{a+1}$; or cycloalkyl having a formula $C_aH_{a-1}$, wherein a is 1, 2, 3, 4, 5, 6, 7, 8, 9, 10, 11, or 12, such as linear or branched alkyl of a formula $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc.; or, cycloalkyl of a formula $C_3H_5$, $C_4H_7$, $C_5H_9$, $C_6H_{11}$, $C_7H_{13}$, $C_8H_{15}$, $C_9H_{17}$, $C_{10}N_{19}$, etc.

With respect to any relevant formula or structural depiction above, some non-limiting examples of $R^2$ may include $R^A$, F, Cl, CN, $OR^A$, $CF_3$, $NO_2$, $NR^AR^B$, $COR^A$, $CO_2R^A$, $OCOR^A$, etc. In some embodiments, $R^2$ may be H; F; or $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^2$ may be H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^2$ may be H.

With respect to any relevant formula or structural depiction above, some non-limiting examples of $R^3$ may include $R^A$, F, Cl, CN, $OR^A$, $CF_3$, $NO_2$, $NR^AR^B$, $COR^A$, $CO_2R^A$, $OCOR^A$, etc. In some embodiments, $R^3$ may be H; F; $C_{1-6}$ alkyl; such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^3$ may be H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^3$ may be H.

With respect to any relevant formula or structural depiction above, some non-limiting examples of $R^4$ may include $R^A$, F, Cl, CN, $OR^A$, $CF_3$, $NO_2$, $NR^AR^B$, $COR^A$, $CO_2R^A$, $OCOR^A$, etc. In some embodiments, $R^4$ may be H; F; $C_{1-6}$ alkyl; such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^4$ may be H.

With respect to any relevant formula or structural depiction above, some non-limiting examples of $R^5$ may include $R^A$, F, Cl, CN, $OR^A$, $CF_3$, $NO_2$, $NR^AR^B$, $COR^A$, $CO_2R^A$, $OCOR^A$, etc. In some embodiments, $R^5$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or phenyl, wherein each phenyl is unsubstituted, or has 1 or 2 substituents independently selected from F and $C_{1-6}$ alkyl. In some embodiments, $R^5$ may be H.

With respect to any relevant formula or structural depiction above, some non-limiting examples of $R^6$ may include $R^A$, F, Cl, CN, $OR^A$, $CF_3$, $NO_2$, $NR^AR^B$, $COR^A$, $CO_2R^A$, $OCOR^A$, etc. In some embodiments, $R^6$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^6$ may be H.

With respect to any relevant formula or structural depiction above, some non-limiting examples of $R^7$ may include $R^A$, F, Cl, CN, $OR^A$, $CF_3$, $NO_2$, $NR^AR^B$, $COR^A$, $CO_2R^A$, $OCOR^A$, etc. In some embodiments, $R^7$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^7$ may be H.

With respect to any relevant formula or structural depiction above, some non-limiting examples of $R^8$ may include $R^A$, F, Cl, CN, $OR^A$, $CF_3$, $NO_2$, $NR^AR^B$, $COR^A$, $CO_2R^A$, $OCOR^A$, etc. In some embodiments, $R^8$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^8$ may be H.

With respect to any relevant formula or structural depiction above, some non-limiting examples of $R^9$ may include $R^A$, F, Cl, CN, $OR^A$, $CF_3$, $NO_2$, $NR^AR^B$, $COR^A$, $CO_2R^A$, $OCOR^A$, etc. In some embodiments, $R^9$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^9$ may be H.

With respect to any relevant formula or structural depiction above, some non-limiting examples of $R^{10}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{10}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{10}$ may be H.

With respect to any relevant formula or structural depiction above, some non-limiting examples of $R^{11}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{11}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{11}$ may be H.

With respect to any relevant formula or structural depiction above, some non-limiting examples of $R^{12}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{12}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{12}$ may be H.

With respect to any relevant formula or structural depiction above, some non-limiting examples of $R^{13}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{13}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{13}$ may be H.

With respect to any relevant formula or structural depiction above, some non-limiting examples of $R^{14}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{14}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{14}$ may be H.

With respect to any relevant formula or structural depiction above, some non-limiting examples of $R^{15}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{15}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{15}$ may be H.

With respect to any relevant formula or structural depiction above, some non-limiting examples of $R^{16}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{16}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{16}$ may be H.

With respect to any relevant formula or structural depiction above, some non-limiting examples of $R^{17}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{17}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{17}$ may be H.

With respect to any relevant formula or structural depiction above, some non-limiting examples of $R^{18}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{18}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{18}$ may be H.

With respect to any relevant formula or structural depiction above, some non-limiting examples of $R^{19}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{19}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{19}$ may be H.

With respect to any relevant formula or structural depiction above, some non-limiting examples of $R^{20}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{20}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{20}$ may be H.

With respect to any relevant formula or structural depiction above, some non-limiting examples of $R^{21}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{21}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{21}$ may be H.

With respect to any relevant formula or structural depiction above, some non-limiting examples of $R^{22}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{22}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{22}$ may be H.

With respect to any relevant formula or structural depiction above, some non-limiting examples of $R^{23}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{23}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{23}$ may be H.

With respect to any relevant formula or structural depiction above, some non-limiting examples of $R^{24}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{24}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{24}$ may be H.

With respect to any relevant formula or structural depiction above, some non-limiting examples of $R^{25}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{25}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{25}$ may be H.

With respect to any relevant formula or structural depiction above, some non-limiting examples of $R^{26}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{26}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{26}$ may be H.

With respect to any relevant formula or structural depiction above, some non-limiting examples of $R^{27}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{27}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{27}$ may be H.

With respect to any relevant formula or structural depiction above, some non-limiting examples of $R^{28}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{28}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{28}$ may be H.

With respect to any relevant formula or structural depiction above, some non-limiting examples of $R^{29}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{29}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{29}$ may be H.

With respect to any relevant formula or structural depiction above, some non-limiting examples of $R^{30}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{30}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{30}$ may be H.

With respect to any relevant formula or structural depiction above, some non-limiting examples of $R^{31}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{31}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{31}$ may be H.

With respect to any relevant formula or structural depiction above, some non-limiting examples of $R^{32}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{32}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{32}$ may be H.

With respect to any relevant formula or structural depiction above, some non-limiting examples of $R^{33}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{33}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{33}$ may be H.

With respect to any relevant formula or structural depiction above, some non-limiting examples of $R^{34}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{34}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{34}$ may be H.

With respect to any relevant formula or structural depiction above, some non-limiting examples of $R^{35}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{35}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{35}$ may be H.

With respect to any relevant formula or structural depiction above, some non-limiting examples of $R^{36}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{36}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{36}$ may be H.

With respect to any relevant formula or structural depiction above, some non-limiting examples of $R^{37}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{37}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{37}$ may be H.

With respect to any relevant formula or structural depiction above, some non-limiting examples of $R^{38}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{38}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{38}$ may be H.

With respect to any relevant formula or structural depiction above, some non-limiting examples of $R^{39}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{39}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{39}$ may be H.

With respect to any relevant formula or structural depiction above, some non-limiting examples of $R^{40}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{40}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{40}$ may be H.

With respect to any relevant formula or structural depiction above, some non-limiting examples of $R^{41}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{41}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{41}$ may be H.

With respect to any relevant formula or structural depiction above, some non-limiting examples of $R^{42}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{42}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{42}$ may be H.

With respect to any relevant formula or structural depiction above, some non-limiting examples of $R^{43}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{43}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{43}$ may be H.

With respect to any relevant formula or structural depiction above, some non-limiting examples of $R^{44}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{44}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{44}$ may be H.

With respect to any relevant formula or structural depiction above, some non-limiting examples of $R^{45}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{45}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{45}$ may be H.

With respect to any relevant formula or structural depiction above, some non-limiting examples of $R^{46}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{46}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{46}$ may be H.

With respect to any relevant formula or structural depiction above, some non-limiting examples of $R^{47}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{47}$ may be H; F; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or phenyl, wherein each phenyl is unsubstituted, or has 1 or 2 substituents independently selected from F and $C_{1-6}$ alkyl. In some embodiments, $R^{47}$ may be H.

With respect to any relevant formula or structural depiction above, such as Formulas 2, 3, 4, 5, 6, 7, and 8, in some embodiments, $R^1$, $R^2$, and $R^3$ are independently H, F, $C_{1-6}$ alkyl, or phenyl, wherein each phenyl is unsubstituted, or has 1 or 2 substituents independently selected from F and $C_{1-6}$ alkyl. In some embodiments $R^1$, $R^2$, and $R^3$ are independently H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^1$, $R^2$, and $R^3$ are H.

With respect to any relevant formula or structural depiction above, such as Formulas 2, 3, 4, 5, 6, 7, and 8, in some embodiments, $R^4$, $R^5$, $R^6$, $R^7$, $R^8$, $R^9$, $R^{10}$, and $R^{11}$ are independently H, F, $C_{1-6}$ alkyl, or phenyl, wherein each phenyl is unsubstituted, or has 1 or 2 substituents independently selected from F and $C_{1-6}$ alkyl. In some embodiments, $R^4$, $R^5$, $R^6$, $R^7$, $R^8$, $R^9$, $R^{10}$, m and $R^{11}$ are independently H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^4$, $R^5$, $R^6$, $R^7$, $R^8$, $R^9$, $R^{10}$, and $R^{11}$ are H.

With respect to any relevant formula or structural depiction above, such as Formulas 2, 3, 4, 5, 6, 7, and 8, in some embodiments, $R^{12}$, $R^{13}$, $R^{14}$, $R^{15}$, $R^{16}$, $R^{17}$, $R^{18}$, and $R^{19}$ are independently H, F, $C_{1-6}$ alkyl, or phenyl, wherein each phenyl is unsubstituted, or has 1 or 2 substituents independently selected from F and $C_{1-6}$ alkyl. In some embodiments, $R^{12}$, $R^{13}$, $R^{14}$, $R^{15}$, $R^{16}$, $R^{17}$, $R^{18}$, and $R^{19}$ are independently H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^{12}$, $R^{13}$, $R^{14}$, $R^{15}$, $R^{16}$, $R^{17}$, $R^{18}$, and $R^{19}$ are H.

With respect to any relevant formula or structural depiction above, such as Formulas 3, 5, 7, and 8, in some embodiments, $R^{27}$, $R^{28}$, $R^{29}$, $R^{30}$, $R^{31}$, $R^{32}$, and $R^{33}$ are independently H, F, $C_{1-6}$ alkyl, or phenyl, wherein each phenyl is unsubstituted, or has 1 or 2 substituents independently selected from F and $C_{1-6}$ alkyl. In some embodiments, $R^{27}$, $R^{28}$, $R^{29}$, $R^{30}$, $R^{31}$, $R^{32}$, and $R^{33}$ are independently H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^{27}$, $R^{28}$, $R^{29}$, $R^{30}$, $R^{31}$, $R^{32}$, and $R^{33}$ are H.

With respect to any relevant formula or structural depiction above, such as Formula 6, in some embodiments, $R^{20}$, $R^{21}$, $R^{22}$, $R^{23}$, and $R^{24}$ are independently H, F, $C_{1-6}$ alkyl, or phenyl, wherein each phenyl is unsubstituted, or has 1 or 2 substituents independently selected from F and $C_{1-6}$ alkyl. In some embodiments, $R^{20}$, $R^{21}$, $R^{22}$, $R^{23}$, and $R^{24}$ are independently H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^{20}$, $R^{21}$, $R^{22}$, $R^{23}$, and $R^{24}$ are H.

With respect to any relevant formula or structural depiction above, such as Formulas 7 and 8, in some embodiments, $R^{20}$, $R^{21}$, $R^{22}$, $R^{23}$, $R^{24}$, $R^{25}$, and $R^{26}$ are independently H, F, $C_{1-6}$ alkyl, or phenyl, wherein each phenyl is unsubstituted, or has 1 or 2 substituents independently selected from F and $C_{1-6}$ alkyl. In some embodiments, $R^{20}$, $R^{21}$, $R^{22}$, $R^{23}$, $R^{24}$, $R^{25}$, and $R^{26}$ are independently H, F, methyl, ethyl, propyl, isopropyl, or phenyl, wherein each phenyl is unsubstituted, or has 1 or 2 substituents independently selected from F, methyl, ethyl, propyl, and isopropyl. In some embodiments, $R^{20}$, $R^{21}$, $R^{22}$, $R^{23}$, $R^{24}$, $R^{25}$, and $R^{26}$ are H.

Some embodiments include the compound:

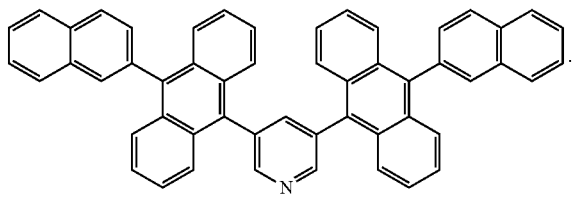 [SMILES: c1ccc2cc(-c3c4ccccc4c(-c4cncc(-c5c6ccccc6c(-c6ccc7ccccc7c6)c6ccccc56)c4)c4ccccc34)ccc2c1]

Some embodiments include a composition useful as a carrier transporting material comprising a compound of any of the formulas herein (hereinafter referred to as "a subject compound"), wherein the compound is characterized by carrier mobility (hole transporting [μh] and/or electron transporting [μe]) of at least about $5 \times 10^{-7}$ cm$^2$/Vs, about $1 \times 10^{-6}$ cm$^2$/Vs, about $5 \times 10^{-6}$ cm$^2$/Vs, or about $1 \times 10^{-6}$ cm$^2$/Vs. In one embodiment, the ph can be about $4.90 \times 10^{-7}$ cm$^2$/Vs and the μe can be about $6.10 \times 10^{-7}$ cm$^2$/Vs. In some embodiments, the carrier mobility may be up to about $1 \times 10^{-3}$ cm$^2$/vs, about $1 \times 10^{-2}$ cm$^2$/Vs, or about 0.1 cm$^2$/Vs, or higher.

Some embodiments include a composition displaying stability under the application of electrical current comprising a subject compound, wherein the compound is characterized by a voltage change in hole only device (dVh) and a voltage change in electron-only device (dVe) of less than 0.5 V, less than 0.3 V, less than 0.2 V, or less than 0.15 V, and which may approach about 0 V, under constant current density of 25 mA/cm$^2$ for 1 hour.

Some embodiments include a composition displaying thermal stability comprising a subject compound, wherein the compound is characterized by a loss of mass of less than about 1% or less than about 5% at a temperature of greater than 375° C., greater than 390° C., greater than 400° C., or greater than 425° C. In some embodiments, the temperature at which the mass of the compound is lost may be determined by thermogravimetric analysis.

Some embodiments include a composition comprising a subject compound. A composition comprising a subject compound may further comprise a fluorescent compound or a phosphorescent compound, and may be useful for light emission in devices such as organic light-emitting devices.

In some embodiments, an organic light-emitting device comprises a subject compound. For example, an organic component comprising a subject compound may be disposed between an anode and a cathode. The organic component may further comprise an emissive layer, wherein a subject compound is in the emissive layer. In some embodiments, the device is configured so that electrons can be transferred from the cathode to the organic component and holes can be transferred from the anode to the organic component.

The subject compounds may have high photostability and thermal stability in organic light-emitting devices. The subject compounds may also have high and well-balanced hole and electron injection rates and mobilities. This may provide OLED devices with high efficiencies and/or long lifetimes. The subject compounds may also form amorphous solids, which may make the compounds easy to form into films.

Some embodiments may have a structure represented by the FIGURE. A hole-transport layer 15 is disposed on the anode 5. A light-emitting (or emissive) layer 20 is disposed on the hole-transport layer 15. An electron-transport layer 30 is disposed on the emissive layer 20, and a cathode 35 is disposed on the electron-transport layer 30.

An anode (e.g., anode 5), may be a layer comprising a conventional material such as a metal, a mixed metal, an alloy, a metal oxide or a mixed-metal oxide, a conductive polymer, and/or an inorganic material such as a carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or, mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). In some embodiments, the anode layer can have a thickness in the range of about 1 nm to about 1000 nm.

A cathode (e.g., cathode 35), may be a layer including a material having a lower work function than the anode layer. Examples of suitable materials for the cathode layer include Group 1 and Group 2 metals, Group 12 metals, including rare earth elements, lanthanides and actinides, materials such as aluminum, indium, calcium, barium, samarium and magnesium, and combinations thereof. Li-containing organometallic compounds, LiF, and Li$_2$O may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

A light-emitting layer (e.g., light-emitting layer 20), may comprise a light-emitting component and a subject compound as a host. The amount of the host in a light-emitting layer may vary. In some embodiments, the amount of a host in a light-emitting layer is in the range of from about 70% to nearly 100% by weight of the light-emitting layer, such as about 90% to about 99%, or about 97% by weight of the light-emitting layer. In some embodiments, the mass of the light-emitting component is about 0.1% to about 10%, about 1% to about 5%, or about 3% of the mass of the light-emitting layer. The light-emitting component may be a fluorescent and/or a phosphorescent compound.

A light-emitting component may comprise an iridium coordination compound such as: bis-{2-[3,5-bis(trifluoromethyl)phenyl]pyridinato-N,C2'}iridium(III)-picolinate; bis (2-[4,6-difluorophenyl]pyridinato-N,C2')iridium (III) picolinate; bis(2-[4,6-difluorophenyl]pyridinato-N,C2')iridium (acetylacetonate); Iridium (III) bis(4,6- difluorophenylpyridinato)-3-(trifluoromethyl)-5-(pyridine-2-yl)-1,2,4-triazolate; Iridium (III) bis(4,6-difluorophenylpyridinato)-5-(pyridine-2-yl)-1H-tetrazolate; bis[2-(4,6-difluorophenyl)pyridinato-N,C2]iridium(III)tetra (1-pyrazolyl)borate; bis[2-(2'-benzothienyl)-pyridinato-N, C3]iridium (III)(acetylacetonate); bis[(2-phenylquinolyl)-N, C2']iridium (III) (acetylacetonate); bis[(1-phenylisoquinolinato-N,C2')]iridium (III) (acetylacetonate); bis[(dibenzo[f,h]quinoxalino-N,C2')iridium (III)(acetylacetonate); tris(2,5-bis-2'-(9',9'-dihexylfluorene)pyridine) iridium (III); tris[1-phenylisoquinolinato-N,C2']iridium (III); tris-[2-(2'-benzothienyl)-pyridinato-N,C3']iridium (III); tris[1-thiophen-2-ylisoquinolinato-N,C3'] iridium (III); tris[1-(9,9-dimethyl-9H-fluoren-2-yl)isoquinolinato-(N,C3')iridium (III)); bis(2-phenylpyridinato-N,C2')iridium (III)(acetylacetonate) [Ir(ppy)$_2$(acac)]; bis(2-(4-tolyl)pyridinato-N,C2')iridium(III)(acetylacetonate) [Ir(mppy)$_2$(acac)]; bis(2-(4-tert-butyl)pyridinato-N,C2')iridium (III)(acetylacetonate) [Ir(t-Buppy)$_2$(acac)]; tris(2-phenylpyridinato-N,C2')iridium (III) [Ir(ppy)$_3$]; bis(2-phenyloxazolinato-N,C2') iridium (III) (acetylacetonate) [Ir(op)$_2$(acac)]; tris(2-(4-tolyl)pyridinato-N,C2')iridium(III) [Ir(mppy)$_3$]; bis[2-phenylbenzothiazolato-N,C2']iridium (III)(acetylacetonate); bis[2-(4-tert-butylphenyl)benzothiazolato-N,C2]iridium (III)(acetylacetonate); bis[(2-(2'-thienyl)pyridinato-N,C3')] iridium (III) (acetylacetonate); tris[2-(9.9 dimethylfluoren-2-yl)pyridinato-(N,C3')]iridium (III); tris[2-(9.9 dimethylfluoren-2-yl)pyridinato-(N,C3')]iridium (III); bis [5-trifluoromethyl-2-[3-(N-phenylcarbzolyl)pyridinato-N, C2]iridium(111)(acetylacetonate); (2-PhPyCz)$_2$Ir(III)(acac); etc.

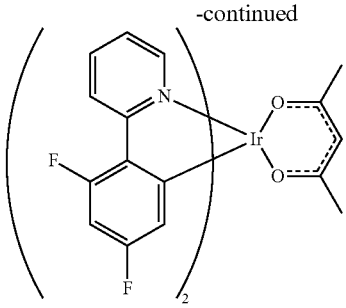

bis-(2-[4,6-difluorophenyl]pyridinato-N,C2')iridium(acetylacetonate) [FIr(acac)]

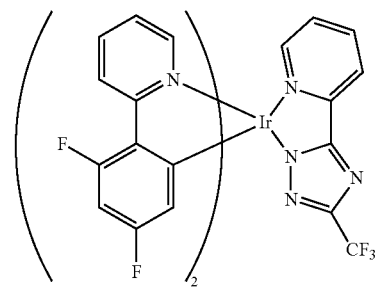

Iridium (III) bis(4,6-difluorophenylpyridinato)-3-(trifluoromethyl)-5-(pyridine-2-yl)-1,2,4-triazolate (FIrtaz)

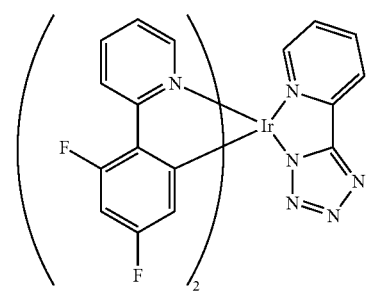

Iridium (III) bis(4,6-difluorophenylpyridinato)-5-(pyridine-2-yl)-1H-tetrazolate (FIrN4)

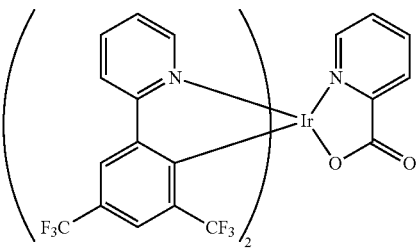

bis-{2-[3,5-bis(trifluoromethyl)phenyl]pyridinato-N,C2'}iridium(III)-picolinate (Ir(CF$_3$ppy)$_2$(Pic)

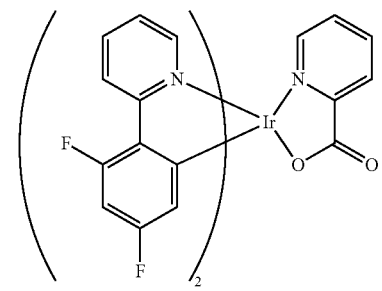

bis-(2-[4,6-difluorophenyl]pyridinato-N,C2')iridium (III) picolinate [FIrPic]

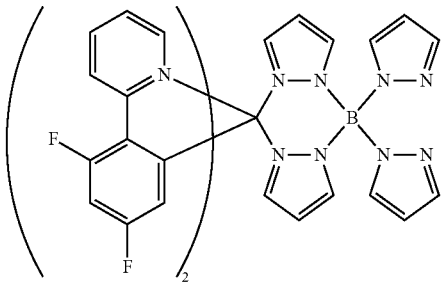

bis[2-(4,6-difluorophenyl)pyridinato-N,C2']iridium(III)tetra(1-pyrazolyl)borate (Fir6)

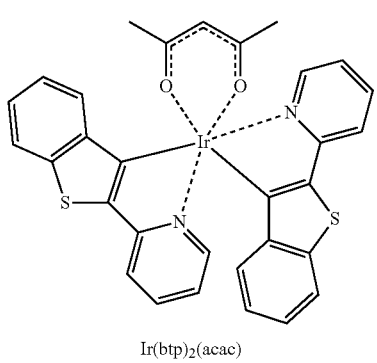
Ir(btp)₂(acac)
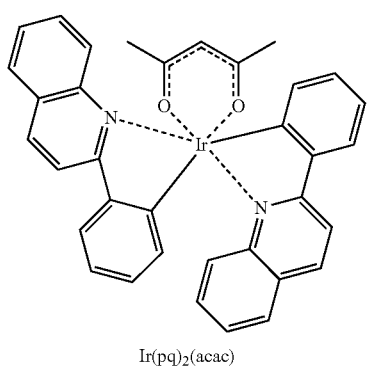
Ir(pq)₂(acac)
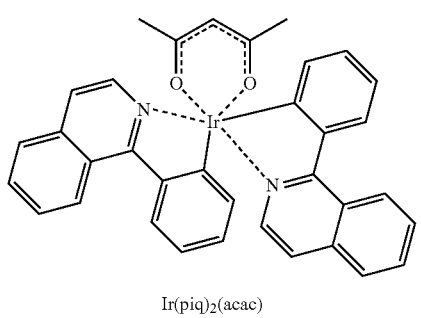
Ir(piq)₂(acac)
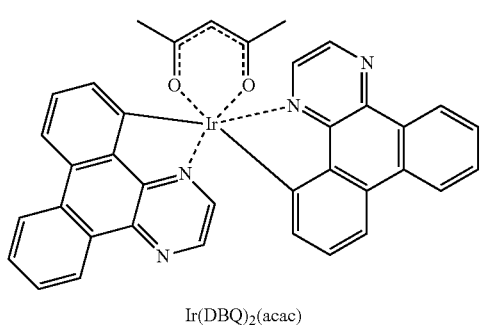
Ir(DBQ)₂(acac)
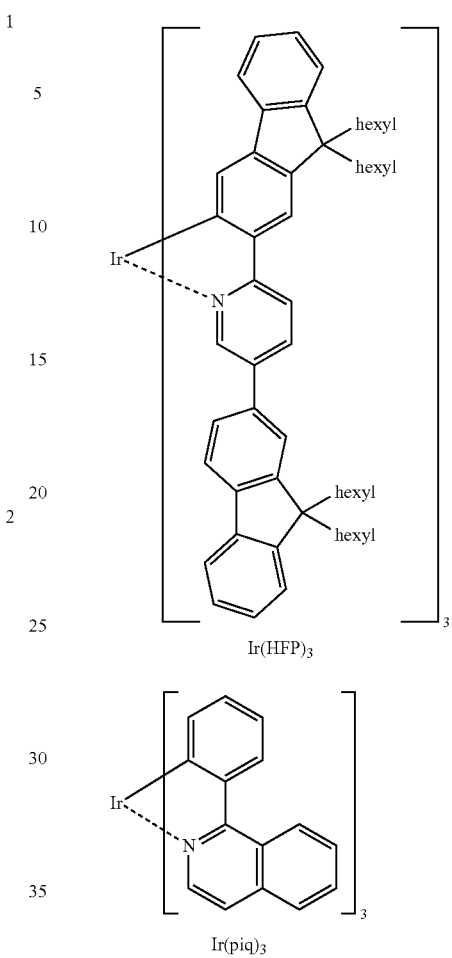
Ir(HFP)₃
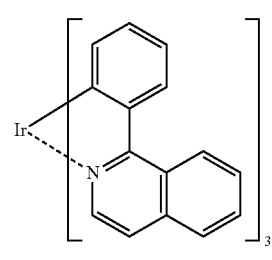
Ir(piq)₃
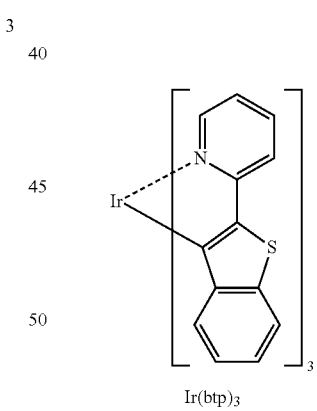
Ir(btp)₃
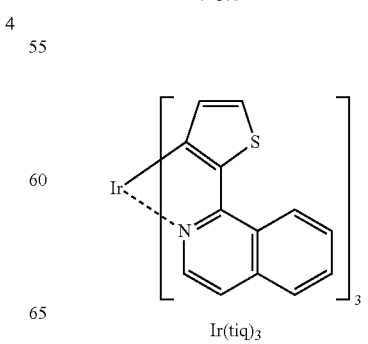
Ir(tiq)₃

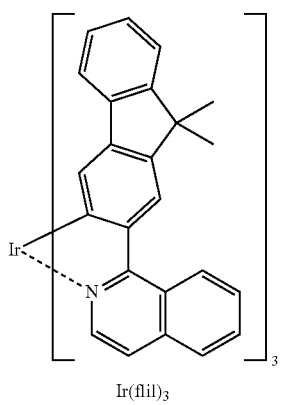

Ir(flil)₃

1. (Btp)₂Ir(III)(acac); bis[2-(2′-benzothienyl)-pyridinato-N,C3′] iridium (III)(acetylacetonate)
2. (Pq)₂Ir(III)(acac); bis[(2-phenylquinolyl)-N,C2′]iridium (III) (acetylacetonate)
3. (Piq)₂Ir(III)(acac); bis[(1-phenylisoquinolinato-N,C2′)]iridium (III) (acetylacetonate)
4. (DBQ)₂Ir(acac); bis[(dibenzo[f, h]quinoxalino-N,C2′)iridium (III)(acetylacetonate)
5. [Ir(HFP)₃], tris(2,5-bis-2′-(9′,9′-dihexyfluorene)pyridine)iridium (III)
6. Ir(piq)₃; tris[1-phenylisoquinolinato-N,C2′]iridium (III)
7. Ir(btp)₃; tris-[2-(2′-benzothienyl)-pyridinato-N,C3′] iridium (III)
8. Ir(tiq)₃; tris[1-thiophen-2-ylisoquinolinato-N,C3′] iridium (III)
9. Ir(fliq)₃; tris[1-(9,9-dimethyl-9H-fluoren-2-yl)isoquinolinato-(N,C3′)iridium (III))

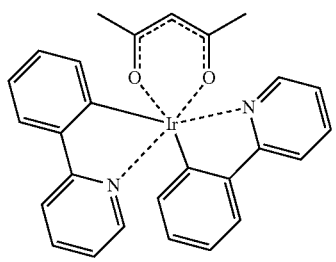

Ir(ppy)₂(acac)

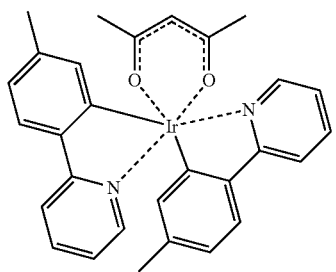

Ir(mppy)₂(acac)

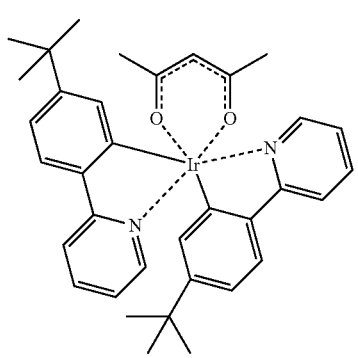

Ir(t-Buppy)₂(acac)

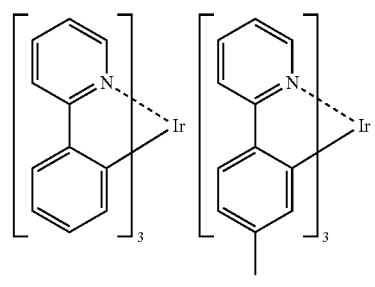

Ir(ppy)₃   Ir(mppy)₃

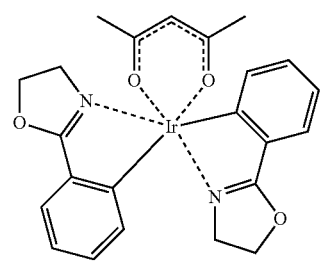

Ir(op)₂(acac)

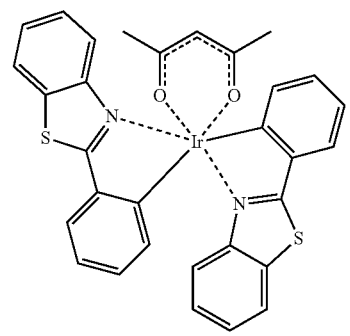

(bt)₂Ir(III)(acac)
bis-[2-phenylbenzothiazolato-
N,C2′]iridium
(III)(acetylacetonate)

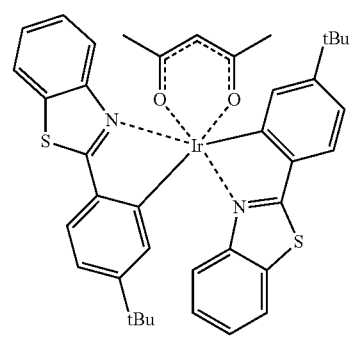

(t-bt)₂Ir(III)(acac)
bis-[2-(4-tert-butylphenyl)benzothiazolato-
N,C2′]iridium(III)(acetylacetonate)

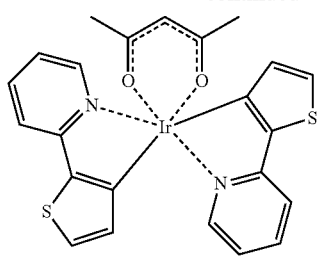

(thp)₂Ir(III)(acac)
bis-[2-(2'-thienyl)pyridinato-
N,C3']iridium(III)
(acetylacetonate)

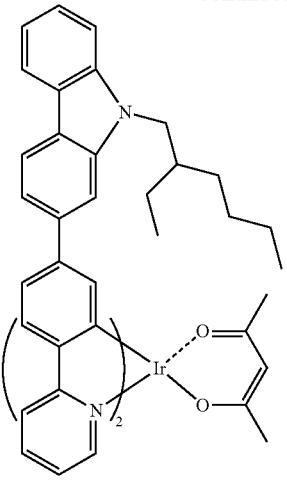

(2-PhPyCz)₂Ir(III)(acac)

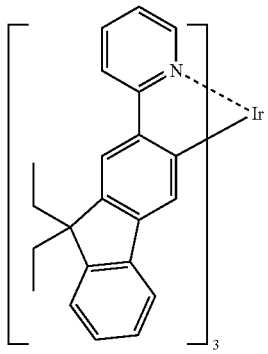

[Ir(Flpy)₃]
tris[2-(9.9-dimethylfluoren-2-
yl(pyridinato-
(N,C3')]iridium(III)

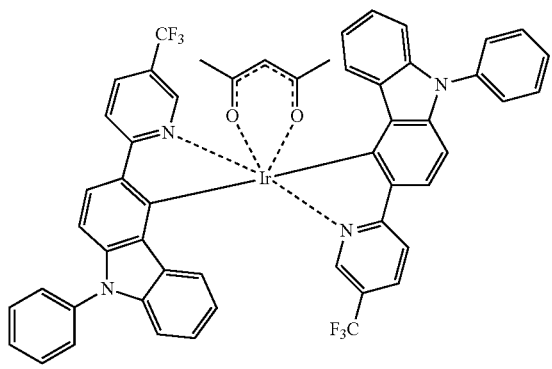

(Cz-CF₃)Ir(III)(acac)
Bis[5-trifluoromethyl-2-[3-(N-
phenylcarbzolyl)pyridinato-
N,C2']iridium(III)(acetylacetonate)

The thickness of a light-emitting layer may vary. In one embodiment, a light-emitting layer has a thickness in the range of from about 1 nm to about 150 nm or about 200 nm.

If present, a hole-transport layer (e.g., hole-transport layer 15), may be disposed between the anode and the light-emitting layer. A hole-transport layer may comprise at least one hole-transport material. Hole-transport materials may include, but are not limited to, an aromatic-substituted amine, a carbazole, a polyvinylcarbazole (PVK), e.g. poly (9-vinylcarbazole); polyfluorene; a polyfluorene copolymer; poly(9,9-di-n-octylfluorene-alt-benzothiadiazole); poly (paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; an oxadiazole; copper phthalocyanine; 1,1-bis(4-bis(4-methylphenyl)aminophenyl) cyclohexane; 2,9-Dimethyl-4,7-diphenyl-1,10-phenanthroline; 3,5-bis(4-tert-butyl-phenyl)-4-phenyl[1,2,4]triazole; 3,4,5-Triphenyl-1,2,3-triazole; 4,4',4'-tris(3-methylphenylphenylamino) triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4',4"-tris (carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); bis[4-(p,p'-ditolyl-amino)phenyl]diphenylsilane (DTASi); 2,2'-bis(4-carbazolylphenyl)-1, t-biphenyl (4Cz-PBP); N,N'N"-1,3,5-tricarbazoloylbenzene (tCP); N,N'-bis (4-butylphenyl)-N,N'-bis(phenyl)benzidine; or the like.

If present, an electron-transport layer (e.g., electron-transport layer 30), may be disposed between the cathode and the light-emitting layer. Examples of electron-transport materials may include, but are not limited to, 2-(4-biphenylyl)-5-(4-tert-butylphenyl)-1,3,4-oxadiazole (PBD); 1,3-bis (N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2, 2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and, 1,3,5-tris[2-N-phenylbenzimidazol-z-yl]benzene (TPBI). In one embodiment, the electron transport layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in a light-emitting device, such as an electron injecting layer (EIL), a hole-blocking layer (HBL), an exciton-blocking layer (EBL), a hole-injecting layer (HIL), etc. In addition to separate layers, some of these materials may be combined into a single layer.

If present, an electron-injecting layer may be between a cathode layer and a light-emitting layer. Examples of suitable material(s) that can be included in the electron injecting layer include but are not limited to, an optionally substituted compound selected from the following: aluminum quinolate (Alq$_3$), 2-(4-biphenyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate)aluminum, and a metal thioxinoid compound such as bis(8-quinolinethiolato) zinc. In one embodiment, the electron injecting layer is aluminum quinolate (Alq$_3$), 2-(4-biphenyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If present, a hole-blocking layer, may be between a cathode and a light-emitting layer. Examples of suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, a light-emitting device can include an exciton-blocking layer. In an embodiment, the band gap of the material(s) that comprise exciton-blocking layer is large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate (Alq$_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

If present, a hole-injecting layer may be between the light-emitting layer and the anode. Examples of suitable hole-injecting material(s) include, but are not limited to, an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4''-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper.

Light-emitting devices comprising a subject compound can be fabricated using techniques known in the art, as informed by the guidance provided herein. For example, a glass substrate can be coated with a high work functioning metal such as ITO which can act as an anode. After patterning the anode layer, a hole-injecting and/or hole-transport layer may be deposited on the anode in that order. A light-emitting layer that includes a light-emitting component, can be deposited on the anode, the hole-transport layer, or the hole-injecting layer. The light-emitting layer may contain a subject compound. An electron-transport layer and/or an electron-injecting layer may deposited in that order on the light-emitting component. The cathode layer, comprising a low work functioning metal (e.g., Mg:Ag), can then be deposited; e.g., by vapor deposition or sputtering. The device may also contain an exciton-blocking layer, an electron blocking layer, a hole blocking layer, a second light-emitting layer, or other layers that can be added to the device using suitable techniques.

Synthetic Examples

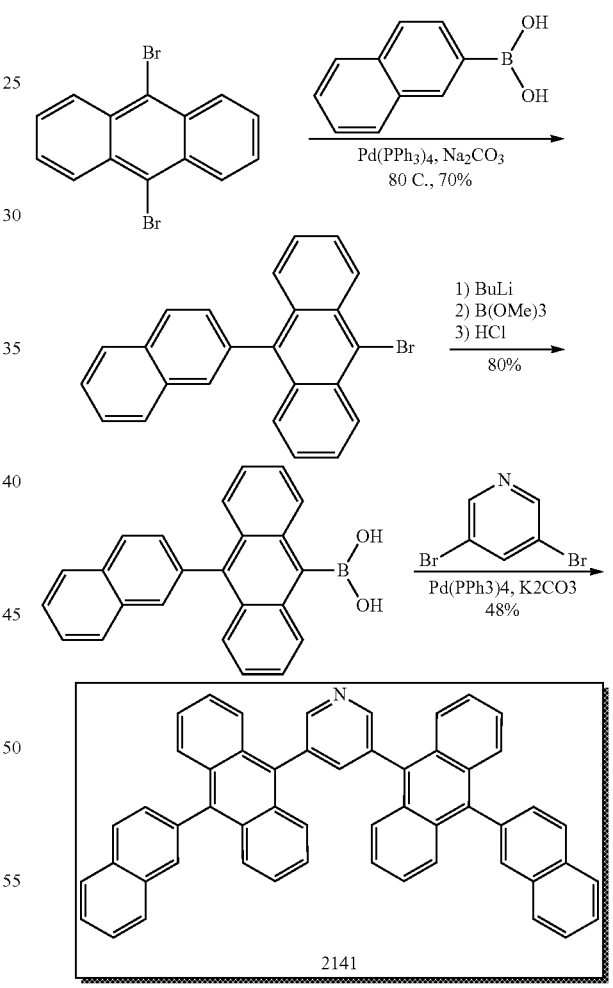

9-Bromo-10-(naphthalen-2-yl)anthracene
(Compound 1)

A mixture of 9,10-dibromoanthracene (16 g, 47.6 mmol), 2-naphthalenyl boronic acid (3.4 g, 19.8 mmol), Pd(PPh$_3$)$_4$ (1.0 g, 0.86 mmol) and sodium carbonate (8.4 g, 79 mmol)

in tetrahydrofuran (THF)/water (200 ml/40 ml) was degassed and heated at about 80° C. for about 3 days. After being cooled to room temperature, the mixture was filtered, and the filtrate was extracted with dichloromethane (DCM) (250 ml), then washed with brine. The organic phase was collected and dried over $Na_2SO_4$, loaded on silica gel, purified by flash column (hexanes) to give a yellow solid (5.7 g, in 74% yield).

10-(Naphthalen-2-yl)anthracen-9-yl)boronic acid (Compound 2

To a solution of 9-bromo-10-(naphthalen-2-yl)anthracene (Compound 1) (3.84 g, 10 mmol) in THF (50 ml) was added n-BuLi solution (1.6 M in hexanes, 7.5 ml) at −78° C. under argon. The mixture was stirred for about 3 hours at −78° C., then freshly distilled trimethylborate (2.5 ml) was added. The whole was then warmed up to room temperature overnight, then 5% HCl aqueous solution (100 ml) was added and stirred for about one day. Filtration gave a white solid (1.7 g), and the filtrate was concentrated and gave a yellow solid, which was washed with hexanes (100 ml×2) which gave a light yellow solid (1.8 g). Total amount of the product was 3.6 g, in 80% yield.

3,5-Bis(10-(naphthalen-2-yl)anthracen-9-yl)pyridine (Host-1)

A mixture of (10-(naphthalen-2-yl)anthracen-9-yl)boronic acid (Compound 2) (1.49 g, 4.28 mmol), 3,5-dibromopyridine (0.507 g, 2.14 mmol), $Pd(PPh_3)_4$ (0.1 g, 0.086 mmol) and potassium carbonate (1.656 g, 12 mmol) in 1,4-dioxane/water (50 ml/5 ml) was degassed and heated at about 90° C. for about 60 hours. After being cooled to room temperature, filtration gave a white solid. After being dried in air, the solid was washed with hot chloroform (250 ml), filtered and dried to give the desired product (0.70 g, in 48% yield, 98.6% purity). The liquid chromatography-mass spectrometry (atmospheric-pressure chemical ionization positive) value calculated for $C_{53}H_{34}N$ [M+H] was 684.3; and as found, was 684.

Analytic Examples: Measuring Charge Mobility

The carrier mobility of an organic thin film was derived from the space charge limited current (SCLC) in the current-voltage (IV) measurement based on the Mott's steady state SCLC model:

$$J = \frac{9\varepsilon\varepsilon_0 \mu V^2}{8L^3},$$

where J is the emission current density, $\varepsilon_0$ is the vacuum permittivity, $\varepsilon$ is the relative permittivity of the organic layer, $\mu$ is the carrier mobility of the organic layer, V is the voltage bias and L is the thickness of the organic layer.

To evaluate the electron and hole mobility of an organic layer, single-carrier devices (i.e., electron-only and hole-only devices) were made. Electron-only devices may have Al/organic layer/LiF/Al structure with Al as the anode and LiF/Al as the cathode. The LiF/Al electrode has a low work function (~2.6 eV) which can facilitate the injection of electrons into the lower-lying lowest unoccupied molecular orbital (LUMO) of the organic layer. By contrast, Al has a relatively lower work function (4.28 eV) than the highest occupied molecular orbital (HOMO) (~5-6 eV) of the organic layer being investigated, which prevents hole injection from the anode. Thus, only electrons are injected into the organic layer and the electron mobility may be measured as the only charge carrier in the organic layer.

The hole-only devices may have the ITO/PEDOT/organic layer/Al with ITO as the anode and Al as the cathode. The high work function of PEDOT (5.2-5.4 eV) facilitates hole injection from the anode into the organic layer. By contrast, the work function (4.28 eV) of Al is higher than the LUMO of the organic layer (2~4 eV), which preventing the electron injection from the cathode. Thus, only holes are injected into the organic layer, and the hole mobility may be measured as the only charge carrier in the organic layer.

Fabrication of electron-only device: A layer of Al was first deposited at a deposition rate of 0.3 nm/s upon a glass substrate (110 nm), the substrate having been cleaned by ultrasound in acetone, and consecutively in 2-propanol, then baked at 110° C. for about 3 hours, followed by treatment with oxygen plasma for about 30 min. In a glove-box hosted vacuum deposition system at a pressure of $10^{-7}$ torr (1 torr=133.322 Pa), Compound Host-1 was then deposited on top of the Al layer at deposition rate of 0.1 nm/s, yielding a 100 nm thick film. LiF (1 nm) and Al (100 nm) were then deposited at a deposition rates of 0.015 nm/s and 0.3 nm/s, respectively.

Fabrication of hole-only device: the ITO coated glass substrate (110 nm) was cleaned by ultrasound in acetone, and consecutively in 2-propanol, baked at 110° C. for about 3 hours, followed by treatment with oxygen plasma for about 30 min. A layer of PEDOT:PSS (HIL 1.1 purchased from H.C. Starck) was spin-coated at 4000 rpm onto the pre-cleaned and $O_2$-plasma treated (ITO)-substrate and annealed at about 180° C. for about 10 min., yielding a thickness of around 30 nm. In a glove-box hosted vacuum deposition system at a pressure of $10^{-7}$ torr (1 torr=133.322 Pa), Compound Host-1 was first deposited on top of the PEDOT:PSS layer at a deposition rate of 0.1 nm/s, yielding a 100 nm thick film. Al was then deposited at a deposition rate of 0.3 nm/s. Each individual device had areas of about 0.08 $cm^2$.

To measure the space charge limited current, a large voltage scan (0-10 V) was applied to each device by a Keithley 2612A sourcemeter (Keithley Instruments, Inc., Cleveland, Ohio, USA) controlled by an Excel add-in software W32-24001VL3-N (Ver.8, Aichiken, Japan). The IV curve was fitted by the SCLC model mentioned above. In addition, the original voltage level applied to the hole only device (VhO (V)) and the change in voltage after 1 hour of time (dVh (V)), and the original voltage level applied to the electron only device (VeO (V)) and the change in voltage after 1 hour of time (dVe (V)), were recorded.

Thermogravimetric analysis (TGA) was used to assess the thermal stability of the material, in which 6.94 mg of the sample was placed in a TGAQ500 thermogravimetric analyzer (TA Instruments, Newcastle, Del., USA) utilizing a 20° C. heating rate up to about 600° C., under $N_2$ gas. The temperature at which 99% (1%) and 95% (5%) of the initial amount of the tested material remained, was recorded.

The results (carrier mobilities, etc.) are depicted in Table 1. All device operation was carried out inside a nitrogen-filled glove-box.

TABLE 1

| Compound | μh (cm²/Vs) | μe (cm²/Vs) | VhO (V) | dVh (V) | VeO (V) | dVe (V) | TGA (1%) | TGA (5%) |
|---|---|---|---|---|---|---|---|---|
| Host-1 | 4.90E−05 | 6.10E−05 | 6.1 | 0.09 | 3.44 | 0.05 | 459° C. | 482° C. |

These data confirm that Host-1 is useful as a carrier transporting material, is stable under the application of electrical current, and/or is thermally stable.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A compound represented by a formula:

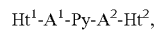

Ht¹-A¹-Py-A²-Ht², wherein Py is pyridin-3,5-yl optionally substituted with 1 or 2 substituents selected from: F, methyl, ethyl, and phenyl;

$A^1$ and $A^2$ are independently anthracen-9,10-yl optionally substituted with 1 or 2 substituents selected from F, methyl, ethyl, and phenyl; and, $Ht^1$ and $Ht^2$ are same and naphthylen-2-yl optionally substituted with 1 or 2 substituents selected from F, methyl, and ethyl;

wherein each phenyl is independently unsubstituted, or has 1 or 2 substituents independently selected from F, methyl, and ethyl.

2. The compound of claim 1, wherein Py is unsubstituted.
3. The compound of claim 1, wherein $A^1$ is unsubstituted.
4. The compound of claim 1, wherein $A^2$ is unsubstituted.
5. The compound of claim 1, wherein $Ht^1$ is unsubstituted.
6. The compound of claim 1, wherein $Ht^2$ is unsubstituted.
7. A compound represented by a formula:

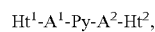

Ht¹-A¹-Py-A²-Ht², wherein Py is optionally substituted pyridin-3,5-yl;

$A^1$ and $A^2$ are unsubstituted anthracen-9,10-yl; and, $Ht^1$ and $Ht^2$ are —NRR°, wherein R and R° are independently optionally substituted $C_{6-10}$ aryl.

8. The compound of claim 7, wherein Py is:

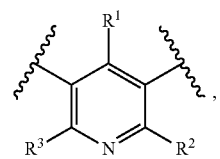

wherein $R^1$, $R^2$, and $R^3$ are independently H, F, methyl, ethyl, propyl, isopropyl, or phenyl, wherein each phenyl is independently unsubstituted, or has 1 or 2 substituents independently selected from F, methyl, ethyl, propyl, and isopropyl.

9. The compound of claim 8, wherein $R^1$, $R^2$, and $R^3$ are H.

10. The compound of claim 7, wherein R and R° are unsubstituted $C_{6-10}$ aryl.

11. The compound of claim 7, wherein Py is unsubstituted, or all substituents of Py have a molecular weight of about 15 g/mol to about 150 g/mol.

12. The compound of claim 1, consisting of:

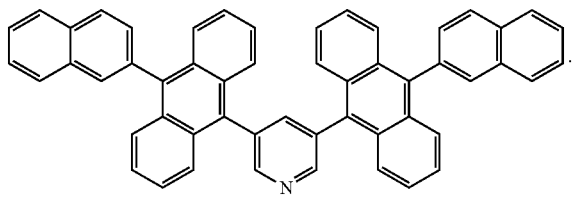 [SMILES: c1ccc2cc(-c3c4ccccc4c(-c4cncc(-c5c6ccccc6c(-c6ccc7ccccc7c6)c6ccccc56)c4)c4ccccc34)ccc2c1]

13. A light-emitting device comprising the compound of claim 1.

14. The light-emitting device of claim 13, wherein the compound is a host in an emissive layer.

15. The light-emitting device of claim 14, wherein the amount of the host is in the range of from about 70% to nearly 100% by weight of the emissive layer.

16. The light-emitting device of claim 15, wherein the amount of the host is in the range of from about 90% to 99% by weight of the emissive layer.

17. The light-emitting device of claim 15, wherein the amount of the host is about 97% by weight of the emissive layer.

18. A light-emitting device comprising the compound of claim 12.

19. The light-emitting device of claim 18, wherein the compound is a host in an emissive layer.

20. The light-emitting device of claim 19, wherein the amount of the host is in the range of from about 70% to nearly 100% by weight of the emissive layer.

21. The light-emitting device of claim 20, wherein the amount of the host is in the range of from about 90% to 99% by weight of the emissive layer.

22. The light-emitting device of claim 20, wherein the amount of the host is about 97% by weight of the emissive layer.

23. A light-emitting device comprising the compound of claim 7.

24. The light-emitting device of claim 23, wherein the compound is a host in an emissive layer.

25. The light-emitting device of claim 24, wherein the amount of the host is in the range of from about 70% to nearly 100% by weight of the emissive layer.

26. The light-emitting device of claim 25, wherein the amount of the host is in the range of from about 90% to 99% by weight of the emissive layer.

27. The light-emitting device of claim 25, wherein the amount of the host is about 97% by weight of the emissive layer.

* * * * *